United States Patent
Kasai et al.

(10) Patent No.: US 7,651,864 B2
(45) Date of Patent: Jan. 26, 2010

(54) COATING SOLUTION FOR GLUCOSE SENSING MEMBRANE AND METHOD OF MANUFACTURING OPTICAL GLUCOSE SENSOR CHIP

(75) Inventors: Shingo Kasai, Yokohama (JP); Kayoko Oomiya, Yokohama (JP); Ikuo Uematsu, Yokohama (JP); Ichiro Tono, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 560 days.

(21) Appl. No.: 11/283,861

(22) Filed: Nov. 22, 2005

(65) Prior Publication Data

US 2006/0134314 A1    Jun. 22, 2006

(30) Foreign Application Priority Data

Nov. 25, 2004  (JP) ............... 2004-340726

(51) Int. Cl.
*G01N 1/31* (2006.01)
*G01N 1/30* (2006.01)
*G01N 1/28* (2006.01)
*G01N 1/00* (2006.01)

(52) U.S. Cl. ............ 436/166; 436/164; 427/2.13; 427/2.11; 427/2.1; 427/162

(58) Field of Classification Search ........ 436/166, 436/530; 205/778; 600/345
See application file for complete search history.

(56) References Cited

U.S. PATENT DOCUMENTS

| 4,774,192 | A | * | 9/1988 | Terminiello et al. ......... 436/530 |
| 4,813,424 | A | * | 3/1989 | Wilkins .................... 600/345 |
| 5,645,710 | A | * | 7/1997 | Shieh ...................... 205/778 |
| 6,078,705 | A | * | 6/2000 | Neuschafer et al. .......... 385/12 |

FOREIGN PATENT DOCUMENTS

JP    9-61346    3/1997

OTHER PUBLICATIONS

Uchiyama et al., Optical Waveguide Type Biochemical Sensor, May 2003. Machine Translation.*

* cited by examiner

*Primary Examiner*—Walter D Griffin
*Assistant Examiner*—Christine T Mui
(74) *Attorney, Agent, or Firm*—Oblon, Spivak, McClelland, Maier & Neustadt, L.L.P.

(57) ABSTRACT

A method of preparing a coating solution for a glucose sensing membrane, the method comprising preserving a first solution containing an oxidizing enzyme or a reducing enzyme of glucose and a reagent for generating a substance for coloring a coloring agent dissolved in a buffer solution, preserving a second solution containing a mixed solution of an alcohol solution of the coloring agent and a solution of a membrane-forming polymer compound, and mixing the first solution and the second solution.

16 Claims, 1 Drawing Sheet

COATING SOLUTION FOR GLUCOSE SENSING MEMBRANE AND METHOD OF MANUFACTURING OPTICAL GLUCOSE SENSOR CHIP

CROSS-REFERENCE TO RELATED APPLICATIONS

This application is based upon and claims the benefit of priority from prior Japanese Patent Application No. 2004-340726, filed Nov. 25, 2004, the entire contents of which are incorporated herein by reference.

BACKGROUND OF THE INVENTION

1. Field of the Invention

The invention relates to a coating solution for a glucose sensing membrane and a method of manufacturing an optical glucose sensor chip.

2. Description of the Related Art

As disclosed in Jpn. Pat. Appln. KOKAI Publication No. 9-61346, an optical glucose sensor chip has a structure including a glass substrate, a pair of gratings formed in the main face of the substrate for receiving and sending light to the substrate, and a glucose sensing membrane having a molecule recognition function and an information conversion function formed on the main face of the substrate between the gratings. The glucose sensing membrane is formed by applying a coating solution for a glucose sensing membrane containing an oxidizing enzyme or a reducing enzyme of glucose, a reagent for generating a substance to be reacted with a coloring agent, a coloring agent, and a membrane-forming polymer compound to an optical waveguide path layer and drying the solution.

The coating solution for a glucose sensing membrane of the glucose sensor chip is conventionally produced by the following first to ninth steps.

The first step: producing an isopropyl alcohol solution containing a coloring agent (e.g. tetramethylbenzidine) in a desired concentration.

The second step: adding isopropyl alcohol to the solution.

The third step: producing a mixed solution by adding pure water to the diluted isopropyl alcohol solution.

The fourth step: adding a buffer agent (e.g. a phosphoric acid buffer) to the mixed solution.

The fifth step: adding an aqueous solution of a reagent (e.g. a peroxidase) generating a substance to be reacted with the coloring agent to the solution obtained in the fourth step.

The sixth step: adding an aqueous solution of a glucose oxidizing enzyme (e.g. a glucose oxidase) to the solution obtained in the fourth step.

The seventh step: shaking the solution obtained in the sixth step up side down.

The eighth step: producing a mixed solution by adding an aqueous solution of a membrane-forming polymer compound (e.g. carboxymethyl cellulose) to the solution shaken up side down.

The ninth step: sufficiently stirring the mixed solution.

However, the conventional method of producing the coating solution for a glucose sensing membrane required a large number of steps and these steps are carried out every time to produce the glucose sensor chip. Therefore, there occurs a problem that the functions may become uneven among production lots.

Because of that, it has been tried to previously produce a large quantity of the coating solution for a glucose sensing membrane so as to avoid dispersion of the functions among production lots. However, the coating solution for a glucose sensing membrane produced in a large quantity has a problem that the activities of the glucose oxidizing enzyme (e.g. glucose oxidase) and the reagent (e.g. peroxidase) generating a substance to be reacted with the coloring agent, which are the components of the coating solution, are decreased during the storage of the coating solution.

BRIEF SUMMARY OF THE INVENTION

According to an aspect of the present invention, there is provided a method of preparing a coating solution for a glucose sensing membrane, the method comprising:

preserving a first solution containing an oxidizing enzyme or a reducing enzyme of glucose and a reagent for generating a substance for coloring a coloring agent dissolved in a buffer solution;

preserving a second solution containing a mixed solution of an alcohol solution of the coloring agent and a solution of a membrane-forming polymer compound; and mixing the first solution and the second solution. Further, according to another aspect of the present invention, there is provided a method of manufacturing an optical glucose sensor chip, comprising:

forming a pair of gratings on a glass substrate for receiving and sending light in the substrate; and forming a glucose sensing membrane by applying the coating solution for a glucose sensing membrane prepared by the method to the substrate region among the gratings and drying the solution.

DETAINED DESCRIPTION OF THE INVENTION

Figure 1:
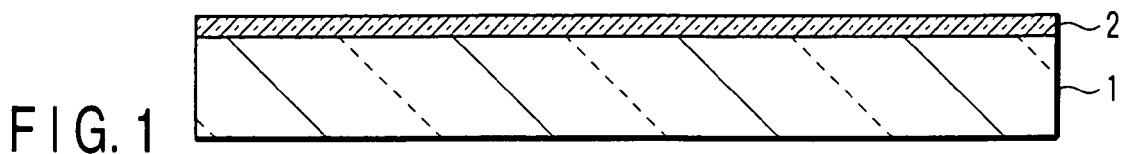
FIGS. 1, 2, 3, 4, 5 and 6 show cross-sectional views showing the production steps of the optical glucose sensor chip according to the second embodiment of the invention.

Hereinafter, a method of preparing a coating solution for a glucose sensing membrane and a method of manufacturing an optical glucose sensor chip of the embodiment according to the invention will be described more in details.

FIRST EMBODIMENT

In the first embodiment, a method of preparing a coating solution for a glucose sensing membrane will be described.

(First Step)

A first solution containing an oxidizing enzyme or a reducing enzyme of glucose and a reagent for generating a substance for coloring a coloring agent dissolved in a buffer solution is stored. Also a second solution obtained by mixing an alcohol solution containing the coloring agent and a solution containing a membrane-forming polymer compound is stored.

The oxidizing enzyme, reagent, and coloring agent may be used in combinations as shown in the following Table 1.

TABLE 1

| Type of glucose | | Reagent for generating substance for coloring agent | Coloring agent |
|---|---|---|---|
| Oxidizing enzyme | Glucose oxidase | Peroxidase | 3,3',5,5'-tetramethylbenzidine N,N'-bis(2-hydroxy-3-sulfopropyl)tolidine 3,3'-diaminodenzidine |
| | Hexokinase | Glucose-6-phosphoric acid dehydrogenase | 3-(4,5-dimethyl-2-thiazolyl)-2,5-diphenyl-2H-tetrazolium bromide 2-(4-rhodophenyl)-3-(2,4-dinitrophenyl)-5-(2,4-disulfophenyl)-2H-tetrazolium 3-3'-[3,3'-dimethoxy-(1,1'-biphenyl)-4,4'-diyl]bis(2,5-diphenyl)-2H-tetrazolium choloride |
| Reducing enzyme | Glucose dehydrogenase | Phosphorus molybdate | Aminobenzoic acid |

Since the oxidizing enzyme (or the reducing enzyme) and the reagent in the first solution have characteristics of easy decomposition by effect of the pH, the buffer solution for buffering the effect of the pH is used as a solvent.

The buffer solution is preferably a phosphoric acid buffer solution and besides, a tris buffer solution may be used.

The above-mentioned first solution is preferable to be stored at a temperature lower than the melting point of the solvent of the solution. If the temperature of the first solution exceeds the melting point of the solvent during the storage, the activity of the enzyme in the solution may possibly be deteriorated.

The alcohol of the second solution may be isopropyl alcohol.

The membrane-forming polymer compound in the second solution may be cellulose type polymer compounds such as carboxymethyl cellulose and hydroxy cellulose. The concentration of the membrane-forming polymer compound of the second solution is preferable to be 0.5% by weight or lower to lower the viscosity of the second solution for making the mixing with the first solution easy.

The second solution is allowed to further contain a phosphoric acid solution for stabilization of the solution.

The second solution is preferable to be stored at 4 to 10° C. If the temperature of the second solution is lower than 4° C. during the storage, the coloring agent may possibly be precipitated during the storage.

With respect to the second solution, the coloring agent, one of the components, may possibly be deteriorated by ultraviolet rays and therefore, the solution is preferable to be stored in an ultraviolet-shutting state, for example, in a dark place or in a brown glass container.

For improvement of the water permeability of the glucose sensing membrane, the coating solution is allowed to further contain an organic compound for making the membrane porous. Examples of an organic compound may include ethylene glycol. The organic compound (e.g. ethylene glycol) may be added to the coating solution by dissolving in an alcohol such as isopropyl alcohol.

When the ethylene glycol dissolved in an alcohol is added to the first solution, the oxidizing enzyme (or the reducing enzyme) and the reagent, which are the components, may become opaque and precipitated in the alcohol and the uniform solubility of these components is inhibited. Therefore, the ethylene glycol dissolved in an alcohol is added to the second solution (containing alcohol such as isopropyl alcohol as a solvent of the coloring agent).

The second solution is preferable to be produced by previously dissolving the above-mentioned membrane-forming polymer compound in pure water, a buffer solution and alcohol such as isopropyl alcohol to be added based on the necessity and stirring and mixing the polymer compound therein to lower the viscosity and then adding and mixing a solution containing the coloring agent. Alternatively, the second solution is allowed to be stored in form of the third solution containing the membrane-forming polymer compound with viscosity suppressed by previous mixing and stirring and the fourth solution containing an alcohol solution of the coloring agent.

(Second Step)

At the time of use, a coating solution for a glucose sensing membrane is produced by mixing the first solution and the second solution. In this case, if the first solution is stored in a temperature lower than the melting point of the solvent in the solution, the first solution is thawed to a temperature approximate to the temperature of the second solution and then mixed with the second solution.

Mixing of the first solution and the second solution can be carried out by stirring and mixing the solutions by a rotating stirring apparatus. The rotating stirring apparatus to be employed may be RLVSD manufactured by ATR (Appropriate Technical Resources).

As described, inventors of the invention have made various kinds of inventions for preventing deterioration of the activity of the enzymes in the case of mass production and storage of the coating solution of a sensing membrane and have tried to keep the activity of the enzymes by preserving the coating solution at a temperature lower than the melting point of the solvent of the solution after the production.

However, it is found that the coloring agent, a component of the coating solution is precipitated and, the enzyme becomes opaque and is precipitated in the co-presence of an alcohol to deteriorate the uniform solubility of the coating solution when the temperature is lowered lower than the melting point of the solvent.

Therefore, the inventors of the invention have made further investigations and accordingly have found that it is made possible to produce easily by simple process the coating solution for a glucose sensing membrane in which the respective components are evenly dissolved and the activity of the enzymes or the like can be maintained by separately producing a group of solutions obtained by dissolving the glucose oxidizing enzyme (or reducing enzyme) whose activity may be deteriorated and the reagent generating a substance to be reacted with the coloring agent in buffer solutions and a group of solutions obtained by dissolving components such as the coloring agent and the membrane-forming polymer compound other than the former in alcohol and pure water; separately storing the former solution (the first solution) and the latter solution (the second solution); and mixing the first solution and the second solution at the time of use.

Accordingly, the first embodiment of the invention makes it possible to produce the coating solution for a glucose sensing membrane suitable for mass production method for an optical glucose sensor chip and to give long term preservation property and stable quality by simple process.

SECOND EMBODIMENT

In the second embodiment, a method of manufacturing an optical glucose sensor chip will be described with reference to drawings of FIGS. 1 to 6.

Figure 2:
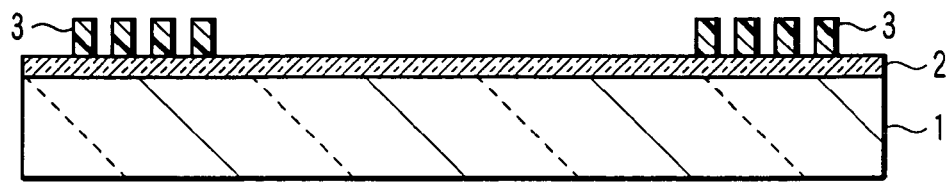
Figure 3:
Figure 4:
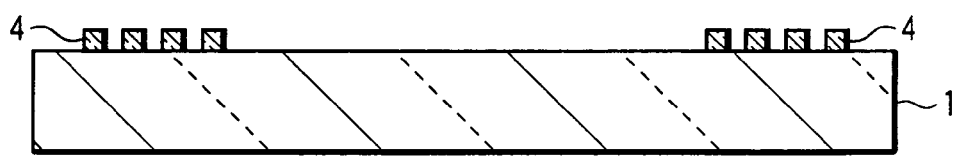

First, as shown in FIG. 1, a titanium oxide film 2 having a refractive index (2.2 to 2.4) higher than a substrate 1 of alkali-free glass with a refractive index of 1.52 is formed on a main face of the substrate 1 by sputtering. As shown in FIG. 2, successively, a resist pattern 3 is formed by applying resist to the titanium oxide film 2, drying the resist, and carrying out lithography. Successively, as shown in FIG. 3, the titanium oxide film is selectively removed by dry etching such as reactive ion etching (RIE) using the resist pattern 3 as a mask to form a grating 4. After that, the resist pattern is removed by ashing (shown in FIG. 4).

Figure 5:
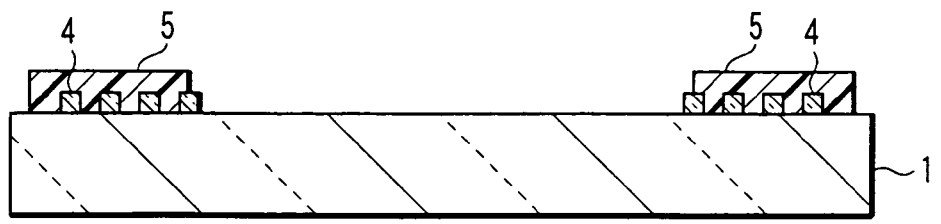

Next, the substrate 1 is dry washed by, for example, oxygen RIE and treated with a coupling agent such as an aminosilane by spin coating and after that, as shown in FIG. 5, a protection film 5 is formed on the grating 4 by screen printing of, for example, fluoro type resin with a low reflective index and non-reactive with the reagent. Next, the substrate 1 is cut by dicing into chip-like form. Since impurities such as the fluoro resin exist on the surface in the sensing membrane formation resin among the grating 4, excimer ultraviolet rays with wavelength of 172 nm are radiated and then the substrate is immersed in an acid solution and washed with pure water. Successively, the first solution described in the first embodiment is thawed to a temperature approximate to the temperature of the second solution and mixed with the second solution to prepare the coating solution for a glucose sensing membrane. The coating solution is dropwise titrated to the sensing membrane formation region and after purging with an inert gas, the solution is dried by vacuum drying to form a glucose sensing membrane 6 and manufacture the optical glucose sensor chip as shown in FIG. 6.

The manufactured chip is preserved in a state that the glucose sensing membrane is kept from a gas in a light-shielding closed bag filled with an inert gas for keeping low humidity.

Figure 6:
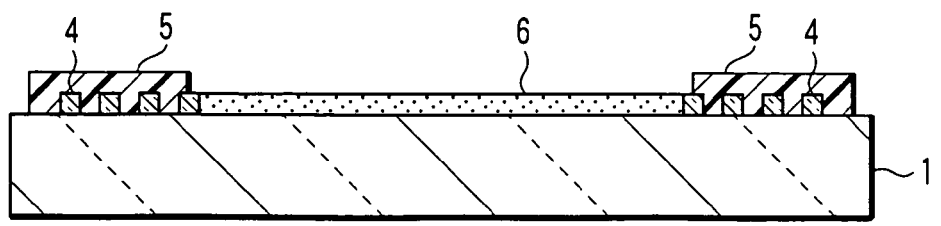

In the glucose sensor chip with the above-mentioned structure, a light source (e.g. semiconductor laser with wavelength of 650 nm) not illustrated and a light receiving device are disposed in the left side and the right side of the back face of the substrate 1 of the glucose sensor chip as shown in FIG. 6. The glucose sensing membrane 6 on the front face of the substrate 1 is brought into contact with glucose of an object to be examined (under the skin of human body). In this case, if the oxidizing enzyme (or the reducing enzyme), the reagent, and coloring agent in a combination, which compose the glucose sensing membrane 6, are glucose oxidase (GOD), peroxidase (POD), and 3,3'-,5,5'-tetramethylbenzidine (TMBZ), glucose is decomposed by GOD to generate hydrogen peroxide; the hydrogen peroxide is decomposed by POD to release active oxygen, and MTBZ is colorized by the active oxygen. That is, the coloring degree of TMBZ is fluctuated in accordance with glucose amount. In such a state, the laser beam from the light source is radiated to the rear face side of the substrate 1 through a polarizing filter and the laser beam is deflected in the interface of the substrate 1 and the grating 4 in the left side and transmitted in the glucose sensing membrane 6 containing the coloring agent colorized in the periphery of the surface of the substrate 1 and the laser beam transmitted by the refraction in the interface of the grating 4 in the right side and the substrate 1 is received by the light receiving device. Following the coloration in the glucose sensing membrane 6 in accordance with the glucose amount, the evanescent wave transmitted in the glucose sensing membrane 6 is absorbed. Therefore, the laser beam intensity is decreased as compared with the light intensity (the initial intensity) received at the time of non-coloration and from the decreased ratio, the glucose amount can be detected.

Hereinafter, the invention will be described more in detail with reference to examples.

EXAMPLE 1

In the Example 1, a first solution and a second solution needed for forming about the glucose sensing membrane 1000 times were prepared.

<Preservation of First Solution>

The first solution with the following composition was produced and stored in frozen state at −20° C.

[First Solution Composition]

A 8 mg/mL Glucose oxidase (GOD) solution (dissolved in 0.01 mol/L phosphoric acid buffer solution (pH:6.0)) 5 mL and A 2 mg/mL peroxidase (POD) solution (dissolved in 0.01 mol/L phosphoric acid buffer solution (pH:6.0)) 10 mL.

<Preservation of Second Solution>

After an aqueous solution containing 2 wt. % of carboxymethyl cellulose (CMC) 80 mL, an isopropyl alcohol solution of 1 wt. % of ethylene glycol 100 mL, isopropyl alcohol (IPA) 90 mL, and a 0.01 mol/L phosphoric acid buffer solution (pH: 6.0) 105 mL were stirred and mixed, a TMBZ solution 100 mL produced by dissolving 3,3',5,5'-tetramethylbenzidine (TMBZ) in a concentration of 1 mg/mL in IPA was added and mixed to obtain the second solution with the following composition and the second solution was stored at 4° C. The CMC concentration in the second solution was 0.5% by weight by addition of IPA and the viscosity was lowered.

[Second Solution Composition]

A 1 mg/mL TMBZ solution (dissolved in IPA) 100 mL, IPA 90 mL

A 0.01 mol/L phosphoric acid buffer solution (pH: 6.0) 105 mL

A 2 wt. % carboxymethyl cellulose (CMC) 80 mL, and

A 1 wt. % ethylene glycol solution (dissolved in IPA) 100 mL.

<Production of Optical Glucose Sensor Chip>

First, a titanium oxide film having a refractive index of 2.2 to 2.4 and a thickness of 50 nm was formed on a main face of an alkali-free glass substrate having a refractive index of 1.52 by sputtering. Successively, a resist pattern was formed by applying resist to the titanium oxide film, drying the resist, and carrying out lithography. Successively, the titanium oxide film was selectively removed by reactive ion etching using the resist pattern as a mask to form a grating 4 and after that, the resist pattern was removed by ashing.

Next, the substrate was dry washed by oxygen RIE and subjected to coupling treatment with an aminosilane by spin coating and after that, a protection film was formed on the grating by screen printing of a fluoro type resin. Next, the substrate was cut by dicing to form chip-like products with 17 mm×6.5 mm size. Excimer ultraviolet rays with wavelength of 172 nm were radiated and then the substrate was immersed in an acid solution and washed with pure water to remove the impurities such as the fluoro resin in the surface of the sensing membrane formation region among the grating.

Successively, the first solution 15 μL stored for 4 weeks was thawed and kept at 4° C. and the thawed first solution was mixed with the second solution 385 μL stored for 4 weeks and stirred and mixed at a rotation speed of 10 rpm for 10 minutes by a rotating and stirring apparatus [RLVSD, manufactured by ATR (Appropriate Technical Resources)] and then heated to a room temperature from 4° C. to prepare a first time coating solution 400 μL for a glucose sensing membrane. The coating solution was then dropwise titrated to the sensing membrane formation region of the substrate 1 and after purging with an inert gas, the solution was dried by vacuum drying to form a porous (water-permeable) glucose sensing membrane with a thickness of 0.5 to 1.5 μm and thus manufacture the optical glucose sensor chip shown in the above-mentioned FIG. 6.

Four optical glucose sensor chips (in total 5) were further manufactured in the same manner.

The second time coating solution for a glucose sensing membrane was produced in the same manner from the first solution and the second solution stored for four weeks and using the coating solution, five optical glucose sensor chips shown in FIG. 6 were manufactured in the same manner.

The manufactured chips were preserved in a state that the glucose sensing membranes were kept from a gas in a light-shielding closed bag filled with an inert gas for keeping low humidity.

COMPARATIVE EXAMPLE 1

A 1 mg/mL TMBZ solution (dissolved in IPA) 100 μL was produced and IPA 110 μL was added to the solution. Pure water 5 μL was added to the diluted IPA solution and then a 0.01 mol/L phosphoric acid buffer solution (pH: 6.0) 50 μL was added to the mixed solution. Successively, an aqueous 2 mg/mL peroxidase (POD) solution 5 μL was added to the obtained solution and further, an aqueous 2 mg/mL glucose oxidase (GOD) solution 40 μL was added. Successively, a 1 wt. % ethylene glycol (dissolved in IPA) 10 μL was added to the solution and then mixed by shaking up side down. Next, an aqueous 2 wt. % carboxymethyl cellulose (CMC) solution 80 μL was added to the solution and mixed by repeating pipetting about 150 times to obtain a coating solution for a glucose sensing membrane.

A porous (water-permeable) glucose sensing membrane with a thickness of 0.5 to 1.5 μm was formed using the above coating solution for a surface grinding method in the same manner as Example 1 and the above-mentioned five optical glucose sensor chips shown in FIG. 6 were manufactured.

The manufactured respective chips were preserved in a state that the glucose sensing membranes were kept from a gas in a light-shielding closed bag filled with an inert gas for keeping low humidity.

The glucose detection by the respective optical glucose sensor chips of Example 1 and Comparative Example 1 was carried out by the following method.

A light source (e.g. semiconductor laser with wavelength of 650 nm) and a light receiving device were disposed in the left side and the right side of the back face of the substrate 1 of each glucose sensor chip as shown in FIG. 6. Without dropping of the glucose solution, the laser beam from the light source was radiated to the rear face side of the substrate 1 through a polarizing filter, deflected in the interface of the substrate 1 and the grating 4 in the left side, and transmitted in the glucose sensing membrane 6 and the laser beam transmitted by the refraction in the interface of the grating 4 in the right side and the substrate 1 was received by the light receiving device and the light intensity (the initial intensity) was detected.

Also, an aqueous glucose solution 0.5 mg/dL was dropwise titrated to the glucose sensing membrane 6 of each glucose sensor chip and the laser light intensity (the measurement intensity) was detected after the laser light was transmitted to the glucose sensing membrane 6 in the periphery of the surface of the substrate 1 in the same manner.

The decrease (sensitivity) ratio of the measurement intensity to the initial intensity of each of the obtained glucose sensor chips, the average value of the decrease ratio (the average of five chips), and CV (the coefficient of variation) of the decrease ratio are shown in Table 2.

The CV (%) was calculated from the equation (1) and if the value is higher, it means that the measurement values are dispersed more.

$$CV(\%) = (\text{standard deviation}/\text{average value}) \times 100 \quad (1)$$

In this equation the standard deviation (s) can be calculated from the following equation (2).

$$s = \sqrt{\frac{1}{n}\sum_{i=1}^{n}(x_i - \bar{x})^2} \quad (2)$$

TABLE 2

| | The number of times of coating solution application | Sample No. | Decrease ratio (%) | Average of decrease ratio (%) | CV (%) |
|---|---|---|---|---|---|
| Example 1 | 1st time | 1 | 7.433 | 7.41 | 0.87 |
| | | 2 | 7.31 | | |
| | | 3 | 7.46 | | |
| | | 4 | 7.47 | | |
| | | 5 | 7.40 | | |
| | 2nd time | 1 | 7.50 | 7.42 | 1.09 |
| | | 2 | 7.30 | | |
| | | 3 | 7.42 | | |
| | | 4 | 7.38 | | |
| | | 5 | 7.48 | | |
| Comparative Example 1 | 1st time | 1 | 7.39 | 7.33 | 2.80 |
| | | 2 | 7.66 | | |
| | | 3 | 7.14 | | |
| | | 4 | 7.24 | | |
| | | 5 | 7.22 | | |

Being clear from Table 2, the glucose sensor chips having the glucose sensing membranes using the coating solution of Example 1 show the decrease ratio about 7%, CV about 0.8%, and are thus found having high sensitivity as that of the glucose sensor chips having the glucose sensing membranes produced using the coating solution of Comparative Example 1 and low sensitivity dispersion.

Also, the decrease ratio and CV are close between groups of glucose sensor chip (each five chips) having the glucose sensing membranes using the coating solution produced first time and second time in Example 1 and it is understood the dispersion is low among production lots.

It is expected that the sensitivity is decreased at the time of detection of glucose in the case of the glucose sensor chips are produced by forming the glucose sensing membranes using the coating solution after the coating solution produced in Comparative Example 1 is preserved for about 4 weeks at around 4° C. It is attributed to, as described above, that activity of GOD and POD, components of the coating solution, is decreased during the preservation and GOD and POD become opaque and precipitated in the co-existence of isopropyl alcohol and thus the uniform solubility is deteriorated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing an optical glucose sensor chip having a glucose sensing membrane containing an oxidizing enzyme or a reducing enzyme of glucose, a reagent for generating a substance for coloring a coloring agent, a coloring agent, and a membrane-forming polymer compound, comprising:
   preparing a first solution by dissolving the oxidizing enzyme or the reducing enzyme of glucose and a reagent for generating a substance for coloring a coloring agent in a buffer solution and then preserving the first solution;
   preparing a second solution by mixing an alcohol solution of the coloring agent and a solution of the membrane-forming polymer compound and then preserving the second solution;
   forming a pair of gratings on a glass substrate for receiving and sending light in the substrate;
   preparing a coating solution for the glucose sensing membrane by mixing the first solution and the second solution before the coating solution is applied to a substrate region among said gratings; and
   forming the glucose sensing membrane by applying the coating solution to the substrate region among the gratings and drying the solution;
   wherein the substrate region among the gratings is subjected to dry washing with excimer ultraviolet rays and wet treatment with an acid solution, before the coating solution is applied to the substrate region among the gratings.

2. The method according to claim 1 wherein the surface of gratings is coated with a protection film containing a fluoro resin.

3. A method of manufacturing an optical glucose sensor chip having a glucose sensing membrane containing an oxidizing enzyme or a reducing enzyme of glucose, a reagent for generating a substance for coloring a coloring agent, a coloring agent, and a membrane-forming polymer compound comprising:
   preparing a first solution by dissolving the oxidizing enzyme or the reducing enzyme of glucose and a reagent for generating a substance for coloring a coloring agent in a buffer solution and then preserving the first solution;
   preparing a second solution by mixing an alcohol solution of the coloring agent and a solution of the membrane-forming polymer compound and then preserving the second solution;
   forming a pair of gratings on a glass substrate for receiving and sending light in the substrate;
   preparing a coating solution for the glucose sensing membrane by mixing the first solution and the second solution before the coating solution is applied to the substrate region among the gratings; and
   forming the glucose sensing membrane by applying the coating solution to the substrate region among the gratings and drying the solution,
   wherein the first solution is preserved at a temperature lower than the melting point of the solvent in the first solution and the second solution is preserved at a temperature of 4° C. to 10° C.

4. The method of claim 3, wherein the surface of the gratings is coated with a protection film containing a fluoro resin.

5. The method according to claim 3, wherein the oxidizing enzyme in the first solution is glucose oxidase, the reagent in the first solution is peroxidase, and the coloring agent in the second solution is 3,3,5,5-tetramethylbenzidine.

6. The method according to claim 3, wherein the membrane-forming polymer compound in the second solution is cellulose type polymer compound.

7. The method according to claim 6, wherein the cellulose type polymer compound is carboxymethyl cellulose or hydroxy cellulose.

8. The method according to claim 3, wherein the second solution further contains an organic compound for making a porous glucose sensing membrane.

9. The method according to claim 8, wherein the organic compound is ethylene glycol.

10. The method of claim 3, wherein said glucose sensing membrane contains an oxidizing enzyme of glucose.

11. The method of claim 3, wherein said glucose sensing membrane contains a reducing enzyme of glucose.

12. The method of claim 3,
    wherein the first solution contains glucose oxidase as an oxidizing enzyme and peroxidase as the substance for coloring a coloring agent; and
    wherein the second solution contains 3,3', 5,5'-tetramethylbenzidine, N,N'-bis(2-hydroxy-3-sulfopropyl)tolidine, and/or 3,3'-diaminodenzidine.

13. The method of claim 3,
    wherein the first solution contains hexokinase as an oxidizing enzyme and glucose-6-phosphoric acid dehydrogenase as the substance for coloring a coloring agent; and
    wherein the second solution contains 3-(4,5-dimethyl-2-thiazolyl)-2,5-diphenyl)-2H-tetrazolium bromide; 2-(4-rhodophenyl)-3 -(2,4-dinitrophenyl)-5-(2,4-disulfophenyl)-2H-tetrazolium, and/or 3-3'-[3,3'-dimethoxy-(1,1'-biphenyl)-4,4'-diyl]bis(2,5-diphenyl)-2H-tetrazolium chloride as the coloring agent.

14. The method of claim 3,
    wherein the first solution contains glucose dehydrogenase as a reducing enzyme and phosphorous molybdate as the substance for coloring a coloring agent; and
    wherein the second solution contains aminobenzoic acid as the coloring agent.

15. A method of manufacturing an optical glucose sensor chip, comprising:
    forming a pair of gratings on a glass substrate for receiving and sending light in the substrate; and
    forming a glucose sensing membrane by applying a coating solution to a substrate region among the gratings and drying the solution;
    wherein the substrate region among the gratings is subjected to dry washing with excimer ultraviolet rays and wet treatment with an acid solution before the coating solution is applied to the substrate region among the gratings; and
    wherein the coating solution is produced at the time of use by mixing:
    a first solution comprising a solvent, a glucose oxidizing enzyme or a glucose reducing enzyme, a reagent for generating a substance for coloring a coloring agent, and a buffer that prevents decomposition of the glucose oxidizing or reducing enzyme, which first solution has been stored at a temperature lower than the melting point of the solvent, with
a second alcohol solution containing a coloring agent and a membrane-forming polymer compound.

16. The method of claim 15, wherein the surface of the gratings is coated with a protection film containing a fluoro resin.

* * * * *